United States Patent [19]

Woolf

[11] Patent Number: 5,422,350

[45] Date of Patent: Jun. 6, 1995

[54] NITROGEN SUBSTITUTED ACRIDINE AND CYTOCHROME P450 INHIBITORS AND METHODS OF USE

[75] Inventor: Thomas F. Woolf, Dexter, Mich.

[73] Assignee: Warner-Lambert Company, Morris Plains, N.J.

[21] Appl. No.: 943,323

[22] Filed: Sep. 10, 1992

[51] Int. Cl.6 .............................................. A61K 31/44
[52] U.S. Cl. .................................... 514/252; 514/297; 514/400
[58] Field of Search ............... 514/252, 297, 400, 252, 514/297, 400

[56] References Cited

U.S. PATENT DOCUMENTS

| | | |
|---|---|---|
| 2,233,970 | 3/1941 | Andersag et al. . |
| 3,659,019 | 4/1972 | Koppe et al. . |
| 3,950,333 | 4/1976 | Durant et al. . |
| 4,352,803 | 10/1982 | Matsumoto et al. . |
| 4,359,578 | 11/1982 | Matsumoto et al. . |
| 4,442,101 | 4/1984 | Ichibashi . |
| 4,631,286 | 12/1986 | Schutske et al. . |
| 4,695,573 | 9/1987 | Shutske et al. . |
| 4,754,050 | 6/1988 | Shutske et al. . |
| 4,816,456 | 3/1989 | Summers .............................. 514/255 |
| 4,835,275 | 5/1989 | Shutske et al. . |
| 4,839,364 | 6/1989 | Shutske et al. ...................... 514/290 |
| 4,999,430 | 3/1991 | Kester et al. . |
| 5,019,395 | 5/1991 | Mahjour et al. . |
| 5,336,485 | 8/1994 | Fariss .................................... 424/10 |

FOREIGN PATENT DOCUMENTS

| | | |
|---|---|---|
| 369388 | 11/1989 | European Pat. Off. . |
| 371388 | 11/1989 | European Pat. Off. . |
| 2091249 | 7/1982 | United Kingdom . |
| 429813 | 11/1974 | U.S.S.R. . |
| 789112 | 12/1980 | U.S.S.R. . |
| 827081 | 5/1981 | U.S.S.R. . |
| 1049065 | 10/1983 | U.S.S.R. . |
| 1156700 | 5/1985 | U.S.S.R. . |
| 1196002 | 12/1985 | U.S.S.R. . |
| 1210789 | 2/1986 | U.S.S.R. . |
| 1416125 | 8/1988 | U.S.S.R. . |
| 1537252 | 1/1990 | U.S.S.R. . |
| 1389050 | 8/1990 | U.S.S.R. . |
| 8902739 | 4/1989 | WIPO . |
| 8902740 | 4/1989 | WIPO . |

OTHER PUBLICATIONS

Selivanova et al., Chemical Abstracts, vol. 98, 209868g, 1983.

"An investigation into the formation of stable, protein-reactive and cytotoxic metabolites from tacrine: in vitro studies with human liver microsomes", Madden et al, Proceedings of the BPS, 14–16 Apr. 1993, British Journal of Clinical Pharmacology, vol. 36, No. 2, Aug. 1993.

"An Investigation Into the Formation of Stable, Protein-Reactive and Cytotoxic Metabolites from Tacrine In Vitro, Studies With Human and Rat Liver Microsomes", Madden et al, Dept. of Pharmacology and Therapeutics, University of Liverpool, Biochemical Pharmacology, vol. 46, No. 1, pp. 13–20, 1993.

"The effect of Buthionine sulphoximine, cimetidine and phenobarbitone on the disposition of amsacrine in the rabbit", J. W. Paxton et al, Cancer Chemotherapy and Pharmacology, 1986, 18:208–212.

"Hepatotoxicity of Tetrahydroaminoacridine in Isolated Rat Hepatocytes: Effect of Gluta-Thione and Vitamin E", Peter Dogterom et al, Biochemical Pharmacology, vol. 37, No. 12, pp. 2311–2313, 1988.

(List continued on next page.)

Primary Examiner—Marianne M. Cintins
Assistant Examiner—William R. A. Jarvis
Attorney, Agent, or Firm—Brooks & Kushman

[57] ABSTRACT

Described is a method of inhibiting the enzymatic metabolism of nitrogen substituted acridines of Formula 1 comprising co-administering with the acridine an effective oxidase inhibiting amount of a P450 1A2 inhibitor. The oxidase is one whose activity is induced by beta-naphthaflavone, 3-methylcholanthrene, arochlor, 2,3,7,8-tetrachlorodibenzo-p-dioxin and isosafrole. The oxidase inhibitor may be a naphthyridine, a xanthine, a phenoxy amino alkane, a carbamoyl imidazole, a heterocyclic guanidine, or a quinoline.

7 Claims, 2 Drawing Sheets

OTHER PUBLICATIONS

"Cytochromes P-450 in Rats: structures, functions, properties and relevant human forms" P. Souck and I. Gut, *Xenobiotica*, 1992, vol. 22, No. 1, 83–103.

"Pharmacokinetic Interactions of Cimetidine 1987" Andrew Somogyi and Murray Muirhead *Clinical Pharmacokinetics* 12: pp. 321–366 (1987).

*Chemical Abstracts*, vol. 63, 1965 Columbus, Ohio Abstract #38 pp. 11537–11538.

*Chemical Abstracts*, 1961 Columbus, Ohio, Abstract #10G pp. 23501–23502.

*Biochemistry*, third edition, Lubert Stryer, Stanford Unversity, W. H. Freeman and Company, New York, pp. 566–568, 1990.

"Tacrine in the Treatment of Alzheimer's Disease: A Clinical Update and Recent Pharmacologic Studies", *Eur. Neurol*, William K. Summers, Ken H. Tachiki, Arthur Kling, 1989:29(suppl. 3):28–32.

"Pharmacological Significance of Acetylcholinesterase Inhibition by Tetrahydroamino-Acridine", Judith K. Marquis, *Biochemical Pharmacolcogy*, vol. 40, No. 5, pp. 1071–1076, 1990.

"Heterogeneity of Hepatic Adverse Reactions to Tetrahydroaminoacridine", Roberts S. K., Gibson P. R., Bhathal P. S., Ames D. J., Davies B., Fraser J. R. E., *Aust N Z MED 20* (Suppl 1):361, 1990.

"Drug Metabolism in Drug-Induced Liver Diseases: Pathogentic Role of Active Metabolites"Tunde Horvath, etc., *Acta Physiologica Hungarica*, vol. 73 (2–3), pp. 293–304 (1989).

"Drug Induced Hepatotoxicity", Neil Kaplowitz, M.D.; Tak Yee Aw,Ph.D.; Francis R. Simon, M.D. Andrew Stolz, M.D., *Annals of Internal Medicine*, 1986:104:826–839.

"Immune Mechanisms in Tienilic Acid Associated Hepatotoxicity", James Neuberger and Roger Williams, *Gut*, 1989, 30, 515–519.

"Substrate Specificities and Functions of the P450 Cytochromes", M. R. Juchau, *Life Sciences*, vol. 47, pp. 2385–2394 (1990).

"A Form of Cytochrome P450 in man.orthologous to form d in the rat.catalyses the O-deethylation of phenacetin and is inducible by cigarette smoking", D. Sesardic, A. R. A. R. Boobis, R. J. Edwards and D. S. Davies, *Br. J. dm Pharmac.* (1988), 26, pp. 363–372.

"Species variation in the response of the cytochrome P450-dependent monooxygenase system to inducers and inhibitors", A. R. Boobis etc., *Xenobiotica*, 1990, vol. 20, No. 11, 1139–1161.

"Induction of Cytochromes P450IA1 and P450IA2 As Determined By Solution Hybridization" Prafulla Raval, Patrick L. Iversen, Edward Bresnick, *Biochemical Pharmacology*, vol. 41 No. 11, pp. 1719–1723, 1991.

"Comparison of Levels of Several Human Microsomal Cytochrome P-450 Enzymes and Epoxide in Normal and Disease States Using Immunochemical Analysis of Surgical Liver Samples" *The Journal of Pharmacology and Experimental Therapeutics*, vol. 256, No. 3, 1189–1194 (1990).

"Oxidation of Toxic and Carcinogenic Chamicals by Human Cytochrome P-450 Enzymes" F. Peter Guengerich, Tsutomu Shimada, *Chem. Res. Toxicol*, vol. 4, No. 4, 1991, pp. 391–407.

"Covalent Binding to Proteins as a Mechanism of Chemical Toxicity", C. Pantarotto, C. Blonda Disease, Metabolism and Reproduction in the Toxic Response to Drugs and Other Chemicals Arch. Toxicol. Suppl. 7, 208–218 (1984).

"Irreversible Protein Binding of (C)imipramine with Rat and Human Liver Microsomes" Herman Kappus and Herbert Remmer, *Biocemical Pharmacoclogy*, vol. 24 pp. 1079–1084 (1975).

"Formation of Cytotoxic Metabolites From Phenytoin, Imipramine, Desipramine, Amitriptyline and Mianserin by Mouse and Human Hepatic Microsomes", Riley, R. J; Roberts P; Kitteringham N.R., Park B.K., *Biochemical Pharacolcogical* 39: 1951–8, 15 Jun. 1990.

"Mechanism of Increased Hepatotoxicity of Acetaminophen by the Simultaneous Administration of Caffeine in the Rat", Chifumi Sato; Namiki Izumi, *The Journal of Pharmacology and Experimental Therapuetics*, vol. 248, No. 3, pp. 1243–1247, 1991.

"Bioactivation of 4-Flourinated Anilines To Benzoquinoneimines As Primary Reaction Products", IMCM Rietjens and J. Vervoort, *Chem-Biol. Interactions*, 77 (1991) 263–281.

"Reactions and Significance of Cytochrome P-450 Enzymes", F. Peter Guengerich, *The Journal of Biological Chemistry*, vol. 266, No. 16, pp. 10019–10022 1991.

"Selectivity in the Inhibition of Mammalian Cytochromes p-450 by Chemical Agents" Michael Murray and Gordon F. Reidy, *Pharmacological Reviews*, vol. 42, No. 2, 1990 85–99.

(List continued on next page.)

OTHER PUBLICATIONS

"Quinoline Inhibition of Cytochrome P-450-Dependent Caffeine Metabolism in human Liver Microsomes", U. Fuhr, etc., *Drug Metabolism and Disposition,* vol. 18, No. 6, pp. 1005–1010, 1991.

"Inhibition of the Oxidative Metabolism of Thyeophylline in Isolated Rat Hepatocytes by the Quinoline Antibiotic Enoxacin and its Metabolite Oxoenoxacin. But not by Ofloxacin", Gerard Mulder, etc., *Biochemical Pharmocology,* vol. 37, No. 13, pp. 2565–2568, 1988.

"Recent developments in Hepatic Drug Oxidation: Implications For Clinical Pharmacokinetics" Kim Brosen, Clin. Pharmacokinet. 18 (3):220–239. 1990.

"Metabolism by Rat Hepatic Microsomes of Flourinated Ether Anesthetics Following Isoniazid Administration" Susan A. Rice,Ph.D., etc., *Anesthesiology,* 53, pp. 489–493, 1980.

"Use of Adult Human Hepatocytes in Primasry Culture For the Study of Clometacin-Induced Immunoallergic Hepatitis" L. Siproudhis, etc., *Toxic. in Vitro,* vol. 5, No. 5/6, pp. 529–534, 1991.

"Isoniazid Potentiation of a Guinea Pig Model of Halothane-associated hepatotoxicity" Richard C. Lind and A. Jay Gandolfi, etc., Society of Toxocology 28th Annual Meeting 1989.

"Mexiletine Metabolism in Vitro by Human Liver", F. Broly, etc., *Drug Metabolism and Dispostion,* vol. 18, No. 3, 1990.

"Disposition of Ethimizol, A Xanthine-related Nootropic Drug, in Perfused Rat Liver and Isolated Hepatocytes" Stefan Bezek, etc., *Drug Metabolism and Disposition,* vol. 18, No. 1, 1990.

"Inhibitors of Cytochrome P-450s and Their Mechanism of Action", Bernard Testa, Peter Jenner, *Drug Metabolism Reviews,* 12(1), 1–117 (1981).

"Drug-Induced Liver Disease", Lewis, J. H., *Current Opinion Gastroenterol* 6(3): 381–90.1990.

"Comparison of the Chromatographic Characteristics of Metabolites of Tacrine Hyrochloride in Human Serum and Urine with Those of In Vitro Metabolic Products From Hepatic Microsomes" *Biochemical Pharmacolcogy,* vol. 42, No. 4, pp. 956–959, 1991.

"Review of Cimetidine Drug Interactions", Eugene M. Sorkin and Diane L. Darvey *Drug Intelligence and Clinical Pharmacy,* vol. 17, 110–120, Feb. 1983.

NITROGEN SUBSTITUTED ACRIDINE AND CYTOCHROME P450 INHIBITORS AND METHODS OF USE

TECHNICAL FIELD

The present invention is concerned with nitrogen substituted acridines and, in particular, their effect on cytochrome P450.

BACKGROUND ART

Nitrogen substituted acridine have been proposed for use in treatment of senile dementia such as Alzheimer's disease. Such materials are described in U.S. Pat. Nos. 4,631,286; 4,695,573; 4,754,050; 4,816,456; 4,835,275; 4,839,364; 4,999,430; and British Patent Appln. 2,091,249, all of which are hereby incorporated by reference.

Clinical studies have been performed on patients suffering from Alzheimer's disease by utilizing tacrine or 1,2,3,4-tetrahydro-9-acridinamine monohydrate monohydrochloride (THA). Serum determinations of patients given THA indicated the very rapid formation of THA metabolites. It has also been indicated that elevations of liver enzymes are found in some patients after THA administration, which reportedly can be controlled by adjustment of medication. W. K. Summers, T. H. Tachiki and A. Kling: "*Tacrine In The Treatment Of Alzheimer's Disease*", EUR. NEUROL. 29 (Supp. 3): 28–32 (1989). Various metabolites of THA have been reported. C. A. Truman, J. M. Ford, C. J. C. Roberts: "*Comparison of the Chromatographic Characteristics of Metabolites of Tacrine Hydrochloride in Human Serum and Urine with those of In Vitro Metabolic Products From Hepatic Microsomes*", BIOCHEMICAL PHARMACOLOGY, Vol. 42, no. 4, pp. 956–959 (1991). THA is extensively metabolized in animals and man to several monohydroxy and dihydroxy metabolites, some of which are excreted as glucuronide derivatives.

Monooxygenation of chemical materials has been ascribed to cytochromes P450 (P450). These hemoprotein containing monooxygenase enzymes displaying a reduced carbon monoxide absorption spectrum maximum near 450 nm have been shown to catalyze a variety of oxidation reactions including hydroxylation of endogenous and exogenous compounds. M. R. Jachau, "*Substrates, Specificities and Functions of the P450 Cytochromes*", LIFE SCIENCES, Vol. 47, pp. 2385–2394 (1990). An extensive amount of research has been conducted on the mechanism's by which P450's can catalyze oxygen transfer reactions. B. Testa and P. Jenner, "*Inhibitors Of Cytochrome P-450s and Their Mechanism of Action*" DRUG METABOLISM REVIEWS, 12(1) 1–117 (1981); F. P. Guengerich, "*Cytochrome P450: Advances and Prospects*", FASEB J., Vol. 6, pp. 667–668 (1992); K. Brosen; M. Murray and C. F. Reidy, "*Recent Developments In Hepatic Drug Oxidation Implications For Clinical Pharmacokinetics*", CLIN. PHARMACOKINET., 18(3): 220–239, 1990; and M. Murray and G. F. Reidy, "*Selectivity in the Inhibition of Mammalian Cytochrome P-450 By Chemical Agents*", PHARMACOLOGICAL REVIEWS, 42, 85–101 (1990).

Murray & Reidy, supra, further state that P-450's are ubiquitous enzymes found in the smooth endoplasmic reticulum as well as mitochondrial fractions of mammalian cells. P450 constitutes a multigene family of enzymes with nearly 150 isoforms identified to date. T. D. Porter and M. J. Coon, "*Cytochrome P-450; Multiplicity of Isoforms, Substrates, and catalytic and Regulatory Mechanisms*", J. BIOL. CHEM., Vol. 266, 13469–13472 (1991). The P450 reaction cycle proceeds briefly as follows: initial binding of a substrate molecule (RH) to the ferric form of the cytochrome results in the formation of a binary complex and a shift in the spin equilibrium of the ferric enzyme from the low- to high-spin state. Some evidence has been presented that suggests this configuration more readily accepts an electron from the flavoprotein reductase to form the ferrous P450 substrate complex. However, not all P450s exhibit a relationship between high-spin content and reduction rate. Indeed, it has been proposed that several factors, including the nature of the P450 substrate, the topography of the enzyme/substrate complex, and the potentials of oxidizable atoms each play a role in regulation of the reduction rate. Molecular oxygen binds to the ferrous P450-substrate complex to form the ferrous dioxygen complex which is then reduced by a second electron from the P450 reductase (or perhaps, in some cases, from reduced nicotinamide adenine dinucleotide via cytochrome $b_5$ and its reductase). Dioxygen bond cleavage in the reduced ferrous dioxygen complex results in the insertion of one atom of oxygen into the substrate, reduction of the other oxygen atom to water, and restoration of the ferric hemoprotein.

Individual members of the P450 family of enzymes and associated mixed function oxidase activities have been described in extrahepatic tissues including brain, adrenal, kidney, testis, ovary, lung and skin. Individual P450s have likewise been characterized in terms of their inducibility by selected chemical classes. Induction of specific P450 enzymes, such as the P450 1A1 and 1A2 subfamily have been extensively studied with respect to regulatory processes of increased mRNA transcription and expression of enzymatic activity. It has been ascertained that materials such as beta-naphthaflavone (beta-NF), 3-methylcholanthrene (3-MC), arochlor 1254 (ACLR) and 2,3,7,8-tetrachlorodibenzo-p-dioxin (TCDD) are materials that have been categorized as inducers of P450 enzymes bearing the designated P450 1A subfamily. At present, two specific P450 enzymes termed 1A1 (nonhepatic) and 1A2 (hepatic) have been characterized by several laboratories. Materials that induce the hepatic P450 1A subfamily of enzymes, and in particular the constitutive 1A2 enzyme include 3-MC, cigarette smoke, beta-NF, TCDD, and ACLR and, in addition, isosafrole, and musk xylenes, are preferential inducers of 1A2. M. Murray and G. F. Reidy, "*Selectivity In The Inhibition Of Mammalian—Cytochromes P450 By Chemical Agents*", PHARMACOLOGICAL REVIEWS, 42, 85–101 (1990); and F. P. Guengerich, "*Characterization of Human Microsomal Cytochrome P-450 Enzymes*", ANNU. REV. PHARMACOL TOXICOL Vol, 29, pp 241–264 (1989).

It is an object of the present invention to improve the metabolic stability of nitrogen substituted acridines in human body fluids (blood, plasma, brain, liver, etc).

It is an object of the present invention to provide in mammalian body fluids a stable concentration of nitrogen substituted acridine.

It is a further object of the present invention to describe and utilize nitrogen substituted acridines in conjunction with inhibitors of cytochrome P450 1A subfamily (1A1 and 1A2) of enzymes.

It is a further object of the present invention to describe nitrogen substituted acridines co-administered with a naphthyridine.

It is a further object of the present invention to describe nitrogen substituted acridines co-administered with a xanthine.

It is a further object of the present invention to describe nitrogen substituted acridines co-administered with a phenoxy amino alkane.

It is a further object of the present invention to describe nitrogen substituted acridines co-administered with a carbamoyl imidazole.

It is a further object of the present invention to describe nitrogen substituted acridines co-administered with a guanidine imidazole, e.g. cimetidine (N-cyano-N'-methyl-N''-[2[[(5-methyl-1H-imidazol-4-yl)methyl]-thio]ethyl]guanidine)

It is a further object of the present invention to describe nitrogen substituted acridines co-administered with a quinoline, e.g. chloroquine (7-chloro-4-(4-diethylamino-1-methylbutylamino)quinoline) and primaquine(8-(4-amino-1-methylbutylamino)-6-methoxyquinoline).

None of the references disclose techniques for maintaining the stability, i.e., non-metabolism of nitrogen substituted acridines, so that they may suitably be effective as agents for treatment of senile dementia.

SUMMARY OF THE INVENTION

The above objects are accomplished by the invention described herein.

Described is a method of inhibiting the enzymatic metabolism of nitrogen substituted acridines by co-administering an effective oxidase inhibiting amount of a P450 1A subfamily inhibitor.

A further embodiment of the invention comprises co-administering with the nitrogen substituted acridine an effective oxidase inhibiting amount of a naphthyridine.

A further embodiment of the invention comprises co-administering with the nitrogen substituted acridine an effective oxidase inhibiting amount of a xanthine.

A further embodiment of the invention comprises co-administering with the nitrogen substituted acridine an effective oxidase inhibiting amount of a phenoxy amino alkane.

A further embodiment of the invention comprises co-administering with the nitrogen substituted acridine an effective oxidase inhibiting amount of a carbamoyl imidazole.

A further embodiment of the invention comprises co-administering with the nitrogen substituted acridine an effective oxidase inhibiting amount of a guanidine imidazole.

A further embodiment of the invention comprises co-administering with the nitrogen substituted acridine an effective oxidase inhibiting amount of a quinoline.

DESCRIPTION OF THE PREFERRED EMBODIMENTS

Figure 1:
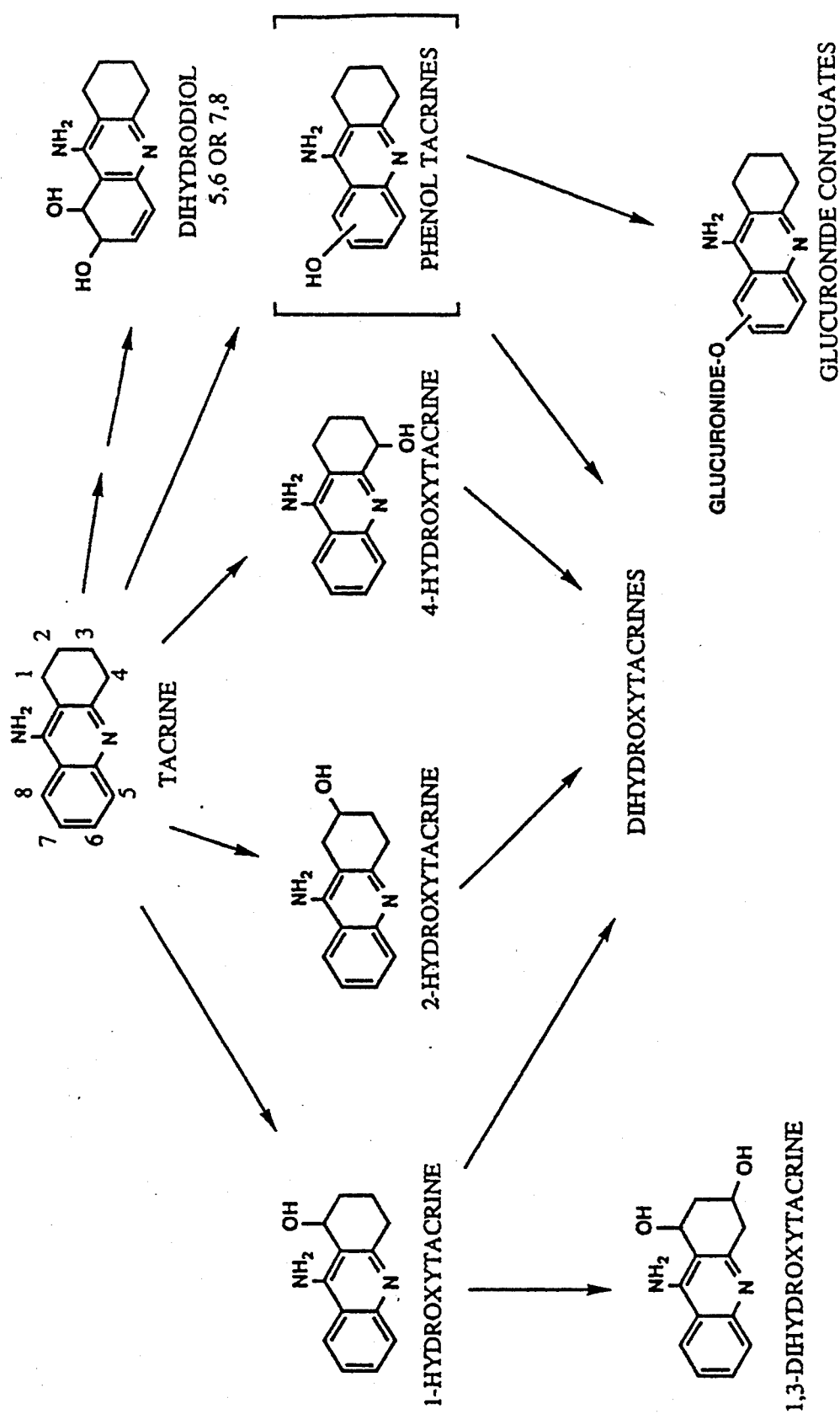
FIG. 1 is a proposed metabolic pathway for tacrine in man.

The present invention is concerned with nitrogen substituted acridines to decrease the amount of or to prevent the metabolism thereof. It has been determined that nitrogen substituted acridines are metabolized by P450 (cytochrome P450) monooxygenase enzymes and, in particular, by the type 1A2 enzyme.

P450s that metabolize the nitrogen substituted or amino acridines as described herein are those enzymes that are induced by materials such as isosafrole, 3-MC, cigarette smoke, beta-NF, TCDD, and ACLR. These P450s belonging to the 1A subfamily, which are hemoprotein containing oxygenases, have their enzymatic activity increased or induced by the aforementioned chemical materials. Therefore, it is desired that these P450 1A2 enzymes located in the liver are hemoproteins whose activity needs to be inhibited in order to prevent the metabolism of the amino acridines as described herein. Applicant, therefore, has characterized the applicable oxygenase P450s both by the general terminology P450 1A2 (cytochrome P450 1A2) but also by the chemical materials that cause or induce the action of these enzymes. Characterization of the specific amino acid sequence for the P450 1A subfamilies in rat and man has been reported. P. Soucek and I. Gut, "Cytochromes P-450 In Rats; Structures, Functions, Properties and Relevant Human Forms", XENOBIOTICA, Vol. 22, pp. 83–103 (1992).

The nitrogen substituted amino acridines which the present invention is concerned and the metabolism which is sought to be decreased or eliminated can be described in U.S. Pat. No. 4,816,456, hereby incorporated by reference. See Formula 1 below:

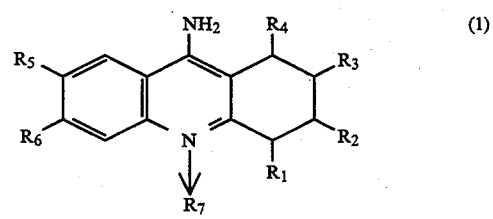

wherein $R_1$ is related from the group consisting of hydrogen, hydroxy, methyl, methoxy, ethyl and ethoxy; $R_1$ and $R_2$ together may form a double bond, $R_3$ and $R_4$ together may form a double bond, or $R_1$, $R_2$, $R_3$ and $R_4$ are all hydrogen; $R_5$ is related from the group consisting of hydrogen, hydroxy, methoxy and ethoxy; $R_6$ is related from the group consisting of hydrogen, hydroxy, methoxy, and ethoxy; and $R_7$ represents no radical; an N-oxy radical; a $C_1$–$C_{20}$ alkyl radical or a radical selected from the group consisting of

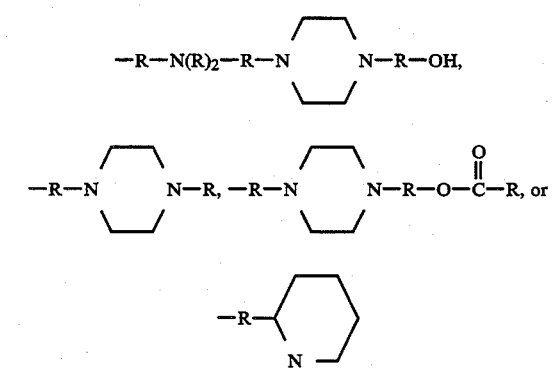

wherein each R is independently selected from $C_1$-$C_{20}$ alkyl; and pharmaceutically acceptable salts thereof.

Nitrogen substituted acridines can also be characterized by the materials described in U.S. Pat. No. 4,999,430, hereby incorporated by reference. See Formula 2.

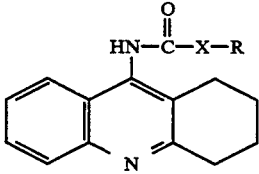

wherein
X is selected from the group consisting of oxygen and $CH_2$; and
R is alkyl of from one to twenty carbon atoms and —$(CH_2)_n$-phenyl,
wherein n is zero or an integer of one to twenty; or a pharmaceutically acceptable acid addition salt thereof.

The nitrogen substituted acridines can also be characterized from the materials described in U.S. Pat. Nos. 4,631,286 and 4,695,573 hereby incorporated by reference. See Formula 3.

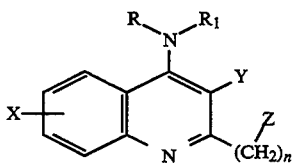

wherein n is 1, 2 or 3; X is hydrogen, lower alkyl, lower alkoxy, halogen, hydroxy, nitro, trifluoromethyl, —$NHCOR_2$ wherein $R_2$ is lower alkyl, or a group of the formula —$NR_3R_4$ wherein $R_3$ and $R_4$ are independently hydrogen or lower alkyl; R and $R_1$ are independently hydrogen, lower alkyl, di-lower alkylamino lower alkyl, aryl lower alkyl, diaryl lower alkyl, furyl lower alkyl, thienyl lower alkyl, oxygen bridged aryl lower alkyl, oxygen bridged diaryl lower alkyl, oxygen bridged furyl lower alkyl, oxygen bridged thienyl lower alkyl, aryl lower alkoxy wherein the aryl group may be unsubstituted or substituted by lower alkyl, lower alkoxy, halogen, hydroxy, trifluoromethyl or diphenyl lower alkyl, unsubstituted or substituted diphenyl lower alkyl wherein the substituents on the phenyl group may be lower alkyl, lower alkoxy, halogen, hydroxy, or trifluoromethyl; Y is —C=O or —C($R_5$)OH wherein $R_5$ is hydrogen or lower alkyl; Z is—$CH_2$— or C=C($R_6$)($R_7$) wherein $R_6$ and $R_7$ are independently hydrogen or lower alkyl; or Y and Z taken together is $CR_5$—CH wherein C($R_5$) and CH correspond to Y and Z respectively; an optical antipode thereof, or a pharmaceutically acceptable acid addition salt thereof, Applicant now wishes to describe the P450 inhibitors that are useful in the present case although it is deemed within the invention herein that any P450 type 1A2 inhibitor may be used in conjunction with the nitrogen substituted acridine as described above.

The first class of the P450 inhibitors that may be utilized are naphthyridines of the type described in U.S. Pat. No. 4,359,578, hereby incorporated by reference. See Formula 4.

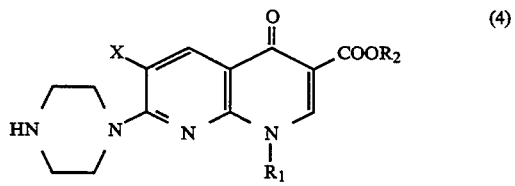

wherein X is a halogen atom, especially a fluorine atom, $R_1$ is an ethyl or vinyl group, and $R_2$ is a hydrogen atom or a lower alkyl group; and nontoxic pharmaceutically acceptable salts thereof.

The preparation of the aforementioned naphthyridines is disclosed in U.S. Pat. No. 4,359,878, the working examples and column 5, line 16 to column 8, line 61.

A potential therapeutic regimen could involve dosing with enoxacin (400 to 800 milligrams per day) for 1 to 2 days (steady state enoxacin plasma concentrations) prior to initiation of tacrine therapy (20–160 mg per day) with coadministration thereafter of tacrine and enoxacin in either a composition product or individual dosage form.

A second class of desirable P450 inhibitors are xanthines described in British specification 2091249, hereby incorporated by reference. See Formula 5.

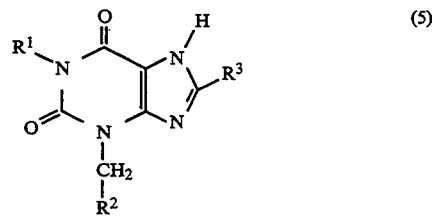

wherein $R^1$ and $R^3$ each independently represent an alkyl group containing from 1 to 6 (preferably at most 4) carbon atoms, and $R^2$ represents a cyclohexenyl, furyl, tetrahydrofuryl or thienyl group, and pharmacologically acceptable salts thereof such as that formed with an alkali metal or a nitrogen-containing organic base.

The preparation of the aforementioned xanthine derivatives are described in British Patent 2,091,249 on page 1, line 38 and following over to page 2, line 44 as well as the working examples.

A potential therapeutic regime could involve dosing with a preferred xanthine, furafylline (1H-purine-2,6-dione, 3-(2-furanylmethyl)-3,7-dihydro-1,8-dimethyl; 300–800 milligrams per day) for 1–2 days (steady state furafylline plasma concentrations) prior to initiation of the preferred amino acridine, tacrine therapy (20–160 milligrams per day) with coadministration thereafter of tacrine and furafylline in either a composition product or individual dosage form.

A further embodiment of a P450 1A2 inhibitor are phenoxy amino alkanes described in U.S. Pat. No. 3,659,019, hereby incorporated by reference. See Formula 6.

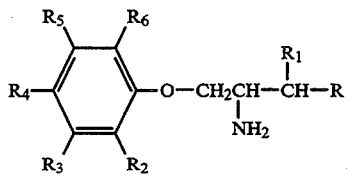

wherein
R is hydrogen or alkyl of 1 to 3 carbon atoms,
$R_1$ is hydrogen or alkyl of 1 to 2 carbon atoms, and
$R_2$ through $R_6$, which may be identical to or different from each other, are each hydrogen or alkyl of 1 to 5 carbon atoms, but preferably 1 to 2 carbon atoms; preferably, however, at least one of $R_1$ through $R_6$ is other than hydrogen and, if $R_1$ and $R_4$ are both methyl, at least one of the remaining substituents R, $R_2$, $R_5$, and $R_6$ is other than hydrogen; or a non-toxic, pharmacologically acceptable acid addition salt thereof.

The method of preparing these compounds is described in U.S. Pat. No. 3,659,019, in particular, Column 2 and Column 3 and the working examples therein which are all herein incorporated by reference.

A potential therapeutic regime could involve dosing with a preferred phenoxy amino alkane such as mexiletine (100–800 milligrams per day) for 1–2 days (steady state mexiletine plasma concentrations) prior to initiation with the preferred amino acridine, namely tacrine (20–160 milligrams per day) with coadministration thereafter of tacrine and mexiletine in either a composition product or individual dosage form.

A fourth P450 type 1A2 inhibitor that is desirable herein is the carbamoyl imidazole of Formula 7.

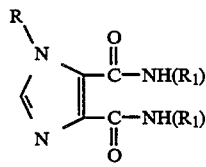

wherein
R is alkyl of from 1 to 20 carbon atoms, preferably lower alkyl of from 1 to 4 carbon atoms, most preferably —$CH_3$; and $R_1$ is independently alkyl of from 1 to 20 carbon atoms, preferably lower alkyl of from 1 to 4 carbon atoms, most preferably —$CH_3$.

The method of preparing these compounds is described in N. B. Vinogradova and N. U. Khromov-Borisov, *Zhur. Obshchei Khim.* 31, 1466–70 (1961) (Chemical Abstracts 55 23501i (1961); and N. B. Vinogradova and N. U. Khromov-Borisov, *Med. Prom. SSSR* 19 (6), 7–13 (1965) (Chemical Abstracts 63 11538d (1965).

A potential therapeutic regime could involve dosing with a preferred carbamoyl imidazole such as ethimizol (100–800 milligrams per day) for 1–2 days (steady state ethimizol plasma concentrations) prior to initiation with the preferred amino acridine, namely tacrine (20–160 milligrams per day) with coadministration thereafter of tacrine and ethimizol in either a composition product or individual dosage form.

An additional P450 type 1A2 inhibitor that is desirable herein is a heterocyclic guanidine of Formula 8:

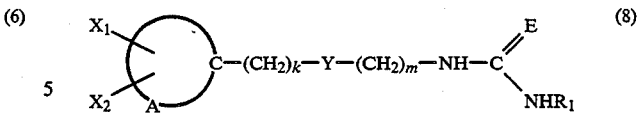

wherein A is such that there is formed together with the carbon atom shown an unsatured heterocyclic nucleus, which comprises at least one nitrogen and may comprise a further hetero atom such as sulphur and oxygen, said unsaturated heterocyclic nucleus, being an imidazole, pyrazole, pyrimidine, pyrazine, pyridazine, thiazole, isothiazole, oxazole, isoxazole, triazole, thiadiazole, benzimidazole or 5,6,7,8-tetrahydroimidazo[1,5-a]pyridine ring; X, is hydrogen, lower alkyl, hydroxyl, trifluoromethyl, benzyl, 15 halogen, amino or $$(CH_2)_4Y(CH_2)_m NH\overset{\overset{E}{\|}}{C}-NHR_1$$

$X_2$ is hydrogen or when $X_1$ is lower alkyl, lower alkyl or halogen; k is 0 to 2 and m is 2 or 3, provided that the sum of k and m is 3 or 4; Y is oxygen, sulphur or NH; E is $NR_2$; $R_1$ is hydrogen, lower alkyl or di-lower alkylamino-lower alkyl; and $R_2$ is hydrogen, nitro or cyano or a pharmaceutically acceptable addition salt thereof. Y is preferably oxygen or sulphur, most advantageously sulphur. Preferably A is such that the nitrogen atom is adjacent to the carbon atom shown and, more preferably, such that it forms with the said carbon atom an imidazole, thiazole or isothiazole ring. Preferably, $X_1$ is hydrogen, methyl, bromo, amino or hydroxyl and $X_2$ is hydrogen. One group of preferred compounds within the present invention is that wherein Y is sulphur, k is 1, m is 2 and $R_1$ is methyl. Specific compounds which are found to be particularly useful are N-cyano-N'-methyl-N''-[2-((4-methyl-5-imidazolyl)-methylthio)ethyl]guanidine, N-cyano-N'-ethyl-N''-[2]((4-methyl-5-imidazolyl)methylthio)ethyl]guanidine, N-cyano-N'-methyl-N''-[2-((4-bromo-5-imidazolyl)-methylthio)ethyl]guanidine. N-cyano-N'-methyl-N''-[2-(2-thiazolylmethylthio)ethyl]-guanidine and N-cyano-N'-methyl-N''-[2-(3-isothiazolylmethylthio)ethyl]-guanidine.

The preparation of the aforementioned compounds is described in U.S. Pat. No. 3,950,333 and particularly, in the working examples herein, and are all incorporated by reference.

A potential therapeutic regime could involve dosing with a preferred heterocyclic guanidine such as cimetidine (100–800 milligrams per day) for 1–2 days (steady state cimetidine plasma concentrations) prior to initiation with the preferred amino acridine, namely tacrine (20–160 milligrams per day) with coadministration thereafter of tacrine and cimetidine in either a composition product or individual dosage form.

Another preferred P450 Type 1A2 inhibitor that is desirably herein is a quinoline of Formula 9:

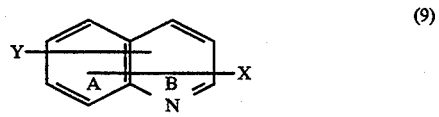

wherein:
Y is an amino group substituted by amino lower alkyl, lower alkyl amino lower alkyl, di-lower alkyl amino lower alkyl, lower alkyl amino, di-lower alkyl amino, lower alkyl substituted by a six-membered nitrogen heterocyclic ring, hydroxy lower alkyl, hydroxy aryl, halogenated lower alkyl;

X is lower alkyl, lower alkoxy, thio lower alkyl, hydroxy lower alkyl, aryl, halogen (such as chloro, bromo or iodo), or lower alkyl mercaptan;

wherein Y may be either in ring A or ring B and X may be present in one or both rings.

Most preferably, the carbon, alpha to the nitrogen in the quinoline ring, is not substituted by an atom other than hydrogen.

The quinolines and the method of preparation are described in U.S. Pat. No. 2,233,970 especially the working examples and page 1, left column, line 35 to the right column, line 40. This patent is hereby incorporated by reference. In addition, see The Merck Index, 11th Ed., published by Merck & Co., Inc. (1989), Reference No. 21634 7751. See also Elderfield et al., *J. AM. CHEM. SOC.*, 68, 1525 (1946); improved procedure: Elderfield et al., ibid, 77, 4816 (1955); Review: *Olenick in ANTIBIOTICS*, Vol. 3, J. W. Corcoran, F. E. Hahn, Eds. (Springer-Verlag, New York 1975), pp. 516–520. Preferred materials are chloroquine and primaquine.

A potential therapeutic regime could involve dosing with a preferred quinoline such as chloroquine or primaquine (100–800 milligrams per day) for 1–2 days (steady state chloroquine or primaquine plasma concentrations) prior to initiation with the preferred aminoacridine, namely tacrine (20–160 milligrams per day) with coadministration thereafter of tacrine and chloroquine or primaquine in either a composition product or individual dosage form.

Listed below are exemplifications of the invention wherein all parts are parts by weight and all degrees are degrees centigrade unless otherwise indicated.

Example 1—In Vivo Metabolism of Tacrine

A single-dose pharmacokinetic and metabolic disposition study was conducted in human male volunteers given [$^{14}$C]tacrine HCl at two dose levels. [$^{14}$C]Tacrine HCl was administered orally to healthy male volunteers at 10-mg (100 μCi) followed by a 40-mg (100 μCi) oral dose 1 month later. Plasma and red blood cells (RBC) were collected predose and for 48 hours postdose. Urine and feces were collected predose and for 96 hours postdose. Urine and plasma samples were analyzed directly by liquid scintillation spectrometry while RBC and fecal samples were solubilized prior to counting. Plasma was assayed for tacrine, 1-hydroxytacrine, 2-hydroxytacrine and 4-hydroxytacrine by a validated HPLC/fluorescence method. Metabolic profiling of urine was performed by HPLC radioactivity detection. Metabolites were identified by HPLC/photodiode array/mass spectrometry.

After oral administration of the 10-mg [$^{14}$C]tacrine HCL dose, mean cumulative urinary and fecal recovery of $^{14}$C activity averaged 56.5% and 23.2% of dose, respectively. Mean total recovery was 79.4%. After a 40-mg dose mean cumulative urinary and fecal recovery of $^{14}$C activity averaged 54.1% and 20.8%, respectively. Mean total recovery was 74.9%.

Time to maximum plasma concentration (tmax) values for plasma radioactivity, tacrine, and each metabolite were approximately 2 hours after administration of both tacrine doses. Mean plasma total radioactivity area under the curve (time zero to last detectable concentration) (AUC(O-tldc)) increased in a dose proportional manner while mean AUC(O-tldc) values for 1-hydroxytacrine, 2-hydroxytacrine, and tacrine increased greater than dose proportionally. Mean AUC(O-tldc) for tacrine, 1-, 2-, and 4-hydroxytacrine comprised approximately 3% and 4% of the total mean plasma radioactivity AUC(O-tldc) for the 10- and 40-mg doses, respectively. In all volunteers, elimination rate of 1-hydroxytacrine from plasma appeared to be limited by the rate of formation.

HPLC radioactivity profiling of urine through 24 hours postdose indicated that tacrine is extensively metabolized with only trace amounts of unchanged drug excreted. Present in the chromatograms were several polar radioactive components accounting for 67% of urinary radioactivity (33% of the dose) with 1-, 4-, and 2-hydroxytacrine accounting for less than 5%, 1%, and 0.5% of the dose, respectively, after administration of either 10 or 40 mg tacrine doses. No apparent differences exist in metabolic profiles at these dose levels and no single metabolite comprised greater than 5% of the dose. FIG. 1 displays a proposed metabolic pathway for tacrine in man. In this same study, a correlation of decreased excretion and lower 1-hydroxytacrine plasma concentrations was observed in subjects who were cigarette smokers as compared to nonsmokers. Human hepatic P450 1A2 has been shown to be inducible by cigarette smoke. D. Sesardic, A. R. Boobis, R. J. Edwards, and D. S. Davies, "*A Form of Cytochrome P450 in Man, Orthologous to Form d in the Rat, Catalyses the O-deethylation of Phenacetin and is Inducible by Cigarette Smoking*", *BR. J. CLIN. PHARMAC.*, Vol. 26, pp. 363–372 (1988).

Cimetidine is an inhibitor of P450 enzymes including P450 1A2. A. Somogyi and M. Muirhead, "*Pharmacokinetic Interactions of Cimetidine*", *CLIN. PHARMACOKIN.*, Vol. 12, pp. 321–366 (1987). In a clinical drug interaction study involving administration of a 40 mg tacrine dose and 300-mg four times a day cimetidine dose, approximately 40% higher plasma concentrations of tacrine and 1-hydroxytacrine were observed as compared to subjects administered tacrine alone.

Concomitant-administration of a single 158-mg dose of theophylline with repeated 20-mg capsule doses of tacrine has resulted in approximately a two-fold increase in theophylline elimination half-life. The major route of theophylline clearance involves metabolism by P450 1A2. M. E. Campbell, D. M. Grant, T. Inaba, and W. Kalow, "*Biotransformation of Caffeine, Paraxanthine, Theophylline, and Theobromine by polycyclic Aromatic Hydrocarbon-Inducible Cytochrome(s) P-450 in Human Liver Microsomes*", *DRUG METAB. DISPOS.* Vol. 15, pp. 237–249 (1987). Therefore, a potential explanation for the theophylline-tacrine clinical interaction is competition for the same P450 1A2 enzymes.

Example 2—In Vitro Metabolism of Tacrine

A series of in vitro metabolism studies have been conducted using human and rat hepatic tissues to investigate the metabolic fate of tacrine as well as to explore the effect of various inducers and inhibitors on tacrine disposition. Incubations of 14C-tacrine (0.5 μM) were conducted for 1 hour with microsomal preparations (app. 1 μM P450) in the presence of NADPH (0.5 mM) and a generating system comprised of 4.0 mM glucose-6-phosphate, 2.0 mM MgCl$_2$, and 1 unit of glucose-6-phosphate dehydrogenase at 37° C. in 0.1M potassium phosphate buffer (pH 7.4). Total reaction volume was 3 mL. Reactions were stopped by freezing in liquid nitrogen or dry-ice acetone. Post reaction incubates were analyzed by HPLC radioactivity detection for tacrine biotransformation products and unchanged drug following precipitation of microsomal protein with either methanol or ethanol (3 volumes). Results are summarized in Table 1. In human liver preparations B and C, tacrine was completely metabolized within 60 min under these incubation conditions. The major product detected was 1-hydroxytacrine with minor amounts of the 2- and 4-hydroxytacrine regioisomers also observed. Incubations with human liver preparation D affected only partial tacrine turnover. Results with rat liver microsomes showed more 1-hydroxytacrine produced as compared to human preparations. Incubations with rat microsomes from phenobarbital (PB) pretreated rats had only a minimal effect on 1-hydroxytacrine formation suggesting that formation of this metabolite is not by the P450 2B (cytochrome P450 IIB or CYP2B) subfamily. D. J. Waxman and L. Axaroff, "*Phenobarbital induction of cytochrome P-450 Gene Expression*", *BIOCHEM J*, Vol. 281, pp. 577–592 (1992); P. Soucek and I. Gut, supra. Isoniazid (I), an inducer of cytochrome P450 2E1 (cytochrome P450 IIE1 or CYP2E1) (D. J. Waxman and L. Axaroff, supra; R. C. Lind, A. J. Gadolfi, P. de la M. Hall: "*Isoniazid Potentiation of a Guinea Pig Model of Halothane-Associated Hepatotoxicity*" *J. TOXICOL* 10 (3): 161–165 (1990); S. A. Rice. L. Sbordone, R. I. Mazze: "*Metabolism by Rat Hepatic Microsomes of Fluorinated Ether Anesthetics Following Isoniazid Administration*" ANESTHESIOLOGY 53: 489–493 (1980)) markedly increased 1-hydroxytacrine formation compared to control rat liver microsomes. Less 1-hydroxytacrine was observed after incubations with MC (P450 1A1 (CYP1A1) and P450 1A2 (CYP-1A2) inducer) induced rat liver microsomes as compared to control, reflecting induction of sequential metabolism (see proposed metabolic pathway in FIG. 1). The amount of 1-hydroxytacrine detected after a 1 hour incubation with MC induced rat microsomes was similar to that observed in human preparations B and C. In a supplimentary study, 1-hydroxytacrine metabolism by P4501A2 was found to be inhibited by co-incubation with tacrine, thereby indicating that sequential tacrine metabolism is also mediated by this specific P450.

TABLE 1

Tacrine and metabolites present in the deproteinized microsomal supernatant fraction after a 60 min incubation of $^{14}$C-tacrine (0.5 μM) catalyzed by human and rat liver microsomes (1 μM P450) in presence of NADPH regenerating system at 37° C.

| | Tacrine nmole equivalents | | | | | |
|---|---|---|---|---|---|---|
| | POLAR UNKS | 2-OH | 1-OH | UNKS | 4-OH | TAC |
| Noninduced Rat | | | | | | |
| w/NADPH | 0.022 | 0.088 | 0.994 | ND | NQ | ND |
| w/out NADPH | ND | ND | ND | ND | ND | 1.22 |
| PB induced Rat | | | | | | |
| w/NADPH | 0.026 | 0.144 | 1.15 | NQ | NQ | ND |
| w/out NADPH | ND | ND | ND | ND | ND | 1.20 |
| I induced Rat | | | | | | |
| w/NADPH | 0.083 | NQ | 1.57 | NQ | NQ | ND |
| w/out NADPH | ND | ND | ND | ND | ND | 1.14 |
| MC induced Rat | | | | | | |
| w/NADPH | 0.009 | NQ | 0.790 | 0.091 | 0.018 | ND |

TABLE 1-continued

Tacrine and metabolites present in the deproteinized microsomal supernatant fraction after a 60 min incubation of $^{14}$C-tacrine (0.5 μM) catalyzed by human and rat liver microsomes (1 μM P450) in presence of NADPH regenerating system at 37° C.

| | Tacrine nmole equivalents | | | | | |
|---|---|---|---|---|---|---|
| | POLAR UNKS | 2-OH | 1-OH | UNKS | 4-OH | TAC |
| w/out NADPH | ND | ND | ND | ND | ND | 1.16 |
| Human Prep B | | | | | | |
| w/NADPH | 0.039 | NQ | 0.750 | 0.146 | 0.039 | ND |
| w/out NADPH | ND | ND | ND | ND | ND | 1.34 |
| Human Prep C | | | | | | |
| w/NADPH | 0.035 | 0.095 | 0.599 | 0.139 | NQ | ND |
| w/out NADPH | ND | ND | ND | ND | ND | 1.07 |
| Human Prep D | | | | | | |
| w/NADPH | ND | ND | 0.201 | ND | ND | 0.803 |
| w/out NADPH | ND | ND | ND | ND | ND | 1.086 |

Figure 2:
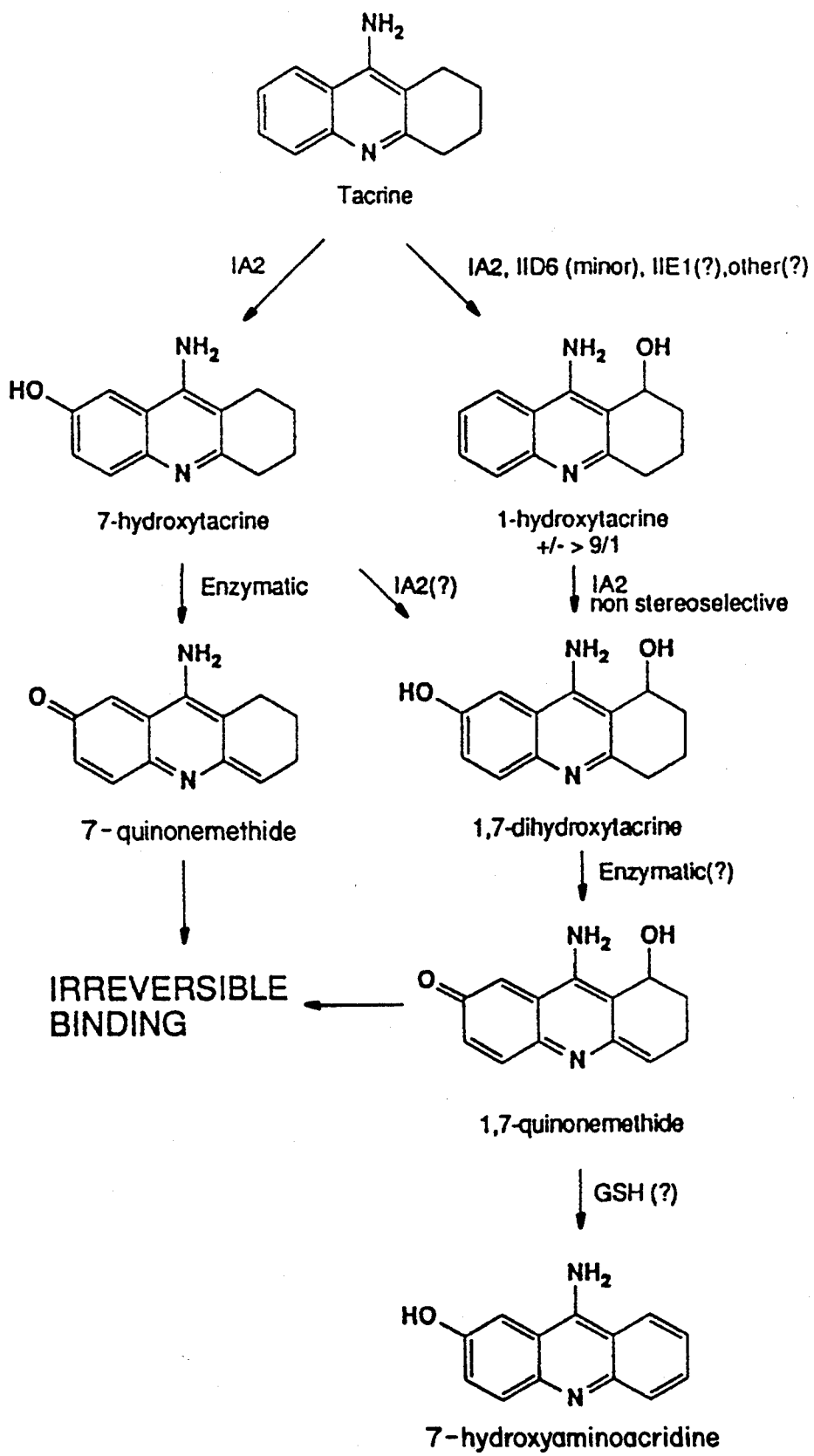
FIG. 2 is a proposed pathway for irreversible binding of tacrine in human liver microsomes.

Pb = Phenobarbital
I = Isoniazid
MC = 3-Methylcholanthrene
NADPH = nicotinamide adenine diphosphate hydride
ND = Not Detectable Example 3—Proposed Pathway For Irreversible Binding Of Tacrine To Human Liver Microsomal Protein Irreversible (nonextractable, presumably covalent) binding of tacrine-derived radioactivity was measured by a slight modification of the method of Martin and Garner. C. N. Martin and R. C. Garner: "*Covalent Binding In Vitro and In Vivo*" in BIOCHEMICAL TOXICOLOGY: *A PRACTICAL APPROACH*, Eds. K. Snell and B. Mullock, IRL, Wash. D.C. pp. 109–126 (1987). Results following exhaustive extraction are displayed in Table 2. Clearly, a high percentage of tacrine was metabolically activated to a reactive intermediate capable of binding to microsomal protein. MC induced rat displayed nearly a 3 fold increase in binding compared to control rat. PB and I pretreatment had little or no effect on binding. The binding of tacrine-derived radioactivity to microsomal protein therefore is not increased by induction of the P450 2B or 2E1 enzymes, respectively. $^{14}$C tacrine incubations which included glutathione (GSH) resulted in a dramatic reduction in irreversible binding whereas incubations with epoxide hydrolase (EH) had only a slight decrease in binding (Table 3). Both GSH and EH failed to produce detectable adducts with the reactive intermediate. Attempts to detect a hydroxylamine metabolite in postreaction incubates with and without ascorbic acid were unsuccessful. These data do not support either an epoxide or hydroxylamine mechanism for activation of tacrine to a reactive species capable of irreversible or covalent binding. A time course study through 1 hour showed tacrine to be rapidly metabolized not only to 1-hydroxytacrine but also to 7-hydroxytacrine. 7-Hydroxytacrine levels rise then fall over time. Thus, 7-hydroxytacrine appears to be a metabolic intermediate which is further metabolized to a putative reactive species capable of irreversible binding to microsomal protein. Based on all of the above information, a potential mechanism responsible for binding is shown in FIG. 2. The reactive quinonemethides formed from either 7-hydroxytacrine or 1,7-dihydroxytacrine are the most likely chemical species capable of the observed irreversible binding to microsomal protein.

TABLE 2

Irreversible protein binding of $^{14}$C-tacrine-derived radioactivity (0.5 μM) catalyzed by human and rat liver microsomes (1 μM P450) in presence of NADPH regenerating system after a 60 min incubation at 37° C. (N = 3).

| | Tacrine equivalents irreversibly bound to 1 mg microsomal protein (nmoles) | |
|---|---|---|
| Noninduced Rat | | |
| with NADPH | 0.041 ± 0.001 | 5.97 ± 0.68 |
| without NADPH | 0.003 | |
| PB induced Rat | | |
| with NADPH | 0.034 ± 0.006 | 4.49 ± 0.85 |
| without NADPH | 0.002 | |
| I induced Rat | | |
| with NADPH | 0.042 ± 0.004 | 4.62 ± 0.73 |
| without NADPH | 0.003 | |
| MC induced Rat | | |
| with NADPH | 0.139 ± 0.010 | 14.5 ± 0.37 |
| without NADPH | 0.003 | |
| Human Prep B | | |
| with NADPH | 0.207 ± 0.014 | 26.9 ± 4.09 |
| without NADPH | 0.003 | |
| Human Prep C | | |
| with NADPH | 0.226 ± 0.005 | 28.8 ± 1.21 |
| without NADPH | 0.003 | |
| Human Prep D | | |
| with NADPH | 0.027 ± 0.002 | 2.96 ± 0.30 |
| without NADPH | 0.003 | |

Percent Bound = Total tacrine mole equivalents bound divided by total substrate times 100
Pb = Phenobarbital
I = Isoniazid
MC = 3-Methylcholanthrene

TABLE 3

Glutathione (GSH) (5 mM) and human liver expoxide hydrase (EH) 100 (ug) effect on irreversible protein binding of $^{14}$C-tacrine (0.5 μM) catalyzed by human liver preparation B and MC inducted rat liver microsomes (1 μM P450) in presence of NADPH regenerating system after a 60 min incubation (N = 3) at 37° C.

| | Tacrine equivalents irreversibly bound to 1 mg microsomal protein (nmoles) | |
|---|---|---|
| MC induced Rat | | |
| NADPH | 0.139 ± 0.010 | — |
| with GSH | 0.058 ± 0.005 | 58.3 |
| with EH | 0.116 ± 0.007 | 16.6 |
| Human Prep B | | |
| NADPH | 0.207 ± 0.014 | — |
| with GSH | 0.031 ± 0.001 | 85.0 |
| with EH | 0.134 ± 0.026 | 35.3 |

Deletion of NADPH from the incubation mixture resulted in no detectable irreversible binding of $^{14}$C-tacrine-derived radioactivity to microsomal protein.
MC = 3-Methylcholanthrene Example 4

To determine if tacrine is a substrate for the polymorphic P450 2D6 enzyme.

A series of experiments were conducted to determine the potential of tacrine to be a substrate for the polymorphic P450 2D6 enzyme. U. A. Meyer, J. Gut, T. Kronbach, C. Skoda, U. T. Meier, and T. Catin, "*The Molecular Mechanisms of Two Common Polymorphisms of Drug Oxidation-Evidence for Functional Changes in Cytochrome P-450 Isozymes Catalysing Bufuralol and Mephenytoin Oxidation*", XENOBIOTICA, Vol. 16, pp 449–464 (1986). Microsomes prepared from intact human liver tissue when incubated up to 60 minutes with $^{14}$C tacrine alone or $^{14}$C tacrine co-incubated with quinidine produced the following results shown in Table 4. Quinidine is an inhibitor of P450 2D6. K. Brosen and L. F. Gram, "*Quinidine Inhibits the 2-Hydroxylation of Imipramine and Desipramine but not the Demethylation of Imipramine*", EUR J CLIN. PHARMACOL., Vol 37, pp 155–160 (1989).

TABLE 4

| | nMoles per 3 mL incubate | | | |
|---|---|---|---|---|
| | Tacrine | | 1-Hydroxytacrine | |
| Quinidine | — | + | — | + |
| Time (min) | | | | |
| 0 | 2.13 | 2.02 | 0 | 0 |
| 5 | 1.24 | 1.22 | 0.416 | 0.383 |
| 10 | 0.831 | 0.816 | 0.716 | 0.606 |
| 20 | 0.302 | 0.401 | 1.03 | 1.067 |
| 40 | 0 | 0.037 | 1.34 | 1.192 |
| 60 | 0 | 0.033 | 1.43 | 1.209 |

Tacrine was metabolized to mainly 1-hydroxytacrine with 7-hydroxytacrine also being observed at incubation times through 40 min. The presence of quinidine did not inhibit the conversion of tacrine to 1-hydroxytacrine. In addition, the irreversible binding of tacrine to human hepatic microsomal proteins was also not effected by this co-incubation. Therefore, the metabolism and irreversible binding of tacrine to microsomal protein is not catalyzed by P450 2D6.

Example 5

To demonstrate the P450 1A2 inhibiting activity, enoxacin, a 1,8 naphthyridine, was tested.

To test the hypothesis that the high affinity (Km less than 5 μM) saturable component of tacrine metabolism in human liver microsomes is by the P450 1A2 enzyme, a time course co-incubation study of $^{14}$C tacrine (0.5 μM) with enoxacin (50 μM), a selective inhibitor of P450 1A2, T. Hasegawa, M. Nadai, T. Kuzuya, I. Muraoka, R. Apichartpichean, K. Takagi, and K. Miyamoto, "*The Possible Mechanism of Interaction between Xanthines and Quinolone*", J. PHARM. PHARMACOL., Vol. 42, pp. 767–772 (1990) was conducted. The results of this study are shown in Table 5. At all time points, the extent of irreversible binding was inhibited by up to 73%. In addition, tacrine's rate of biotransformation was markedly inhibited (5 to 6 fold). Therefore, a specific P450 1A2 inhibitor can not only decrease the rate of irreversible binding but also inhibit the overall rate of tacrine biotransformation. The effect of various enoxacin concentrations (8, 20, and 50 μM) on the extent of irreversible binding was examined in a separate study. Results are presented in Table 6. The greatest inhibition of tacrine irreversible binding and biotransformation was achieved with co-incubation with 50 μM enoxacin.

Since 1-hydroxytacrine was found to bind irreversibly (nonextractable, presumably covalent) to human microsomal protein, the role of P450 1A2 in the metabolic activation step was examined by co-incubating $^{14}$C 1-hydroxytacrine with various concentrations of enoxacin (8, 20, and 50 μM). Table 6 displays results confirming the inhibitory effect of enoxacin on the binding of 1-hydroxytacrine which supports the involvement of P450 1A2 in its activation pathway.

TABLE 5

The effect of 50 μM enoxacin on the irreversible binding of 0.5 μM tacrine-derived radioactivity to human microsomal (1 μM P450) protein with time in the presence of a NADPH regenerating system at 37° C.

| | | Tacrine Equivalents irreversibly bound to 1 mg microsomal protein | |
|---|---|---|---|
| | Time (min) | (nmoles) | Percent Inhibition |
| Tacrine | 5 | 0.022 ± 0.005*, ** | |
| | 10 | 0.048 ± 0.006 | |
| | 20 | 0.096 ± 0.006 | |
| | 45 | 0.148 ± 0.024 | |
| Tacrine + | 5 | 0.009 ± 0.002 | 59.1 |
| Enoxacin | 10 | 0.017 ± 0.003 | 64.5 |
| | 20 | 0.026 ± 0.002 | 72.9 |
| | 45 | 0.052 ± 0.006 | 64.9 |

*N = 3
**SD

TABLE 6

Irreversible binding of 14C-tacrine or 14C-1-hydroxytacrine-derived radioactivity to human microsomal protein (1 μM cytochrome P450) in the presence of various concentrations of enoxacin and a NADPH regenerating system following a 20 min incubation at 37° C.

| | | Tacrine or 1-hydroxytacrine equivalents irreversibly bound to 1 mg microsomal protein | |
|---|---|---|---|
| Tacrine (0.3 μM) | Enoxacin (1 μM) | | |
| | 0.0 | 0.040   0.001*, ** | — |
| | 8.0 | | 14.4 |
| | 20.0 | 0.036 ± 0.008 | 29.8 |
| | 50.0 | 0.028 ± 0.001 | 43.4 |
| | | 0.023 ± 0.002 | |
| 1-Hydroxytacrine (0.5 μM) | 0.0 | 0.018 ± 0.001 | — |
| | 8.0 | 0.017 ± 0.001 | 8.2 |
| | 20.0 | 0.014 ± 0.001 | 22.2 |
| | 50.0 | 0.009 ± 0.001 | 51.7 |

Deletion of NADPH from the incubation mixture resulted in no irreversible binding of $^{14}$C-tacrine derived radioactivity or $^{14}$C-1-hydroxytacrine to microsomal protein.
*N = 3
**SD

Example 6

The potential for other P450 1A2 inhibitors, namely furafylline and ethimizol to inhibit the irreversible binding of $^{14}$C tacrine and $^{14}$C 1-hydroxytacrine were examined in a MC induced rat hepatocyte study. Results in terms of percent of tacrine-derived radioactivity binding as determined in tacrine alone incubates are presented in Table 7. Furafylline was the most effective inhibitor of irreversible binding for both tacrine and 1-hydroxytacrine while ethimizol and enoxacin had less of an effect. These data support the concept that other specific P450 1A2 inhibitors besides enoxacin can affect the rate of tacrine and 1-hydroxytacrine metabolism as well as irreversible binding.

TABLE 7

The effect of enoxacin, ethimizol, furafylline, and glutathione on the irreversible binding of 14C-tacrine and 14C-1-hydroxytacrine-derived radioactivity to hepatocytes from MC induced male rats.

| | Percent Control Value |
|---|---|
| Tacrine (10 uM) | |
| + Enoxacin (50 uM) | 78.9 |
| + Ethimizol (50 uM) | 80.1 |
| + Furafylline (50 uM) | 31.6 |
| + Glutathione (5 mM) | 62.6 |
| 1-Hydroxytacrine (10 uM) | |

TABLE 7-continued

The effect of enoxacin, ethimizol, furafylline, and glutathione on the irreversible binding of 14C-tacrine and 14C-1-hydroxytacrine-derived radioactivity to hepatocytes from MC induced male rats.

| | Percent Control Value |
|---|---|
| + Enoxacin (50 uM) | 79.8 |
| + Ethimizol (50 uM) | 65.6 |
| + Furafylline (50 uM) | 31.7 |
| + Glutathione (5 mM) | 49.1 |

Example 7

The antimalarial agents chloroquine and primaquine were examined in rat liver microsomes by Back et al. (1983) and found to be inhibitors of ethoxyresorufin O-deethylase activity. D. J. Back, H. S. Purba, C. Staiger, M. L. Orme, A. M. Breckenridge, "Inhibition of Drug Metabolism by the Anti Malarial Drugs Chloroquine and Primaquine in the Rat", BIOCHEM. PHARMACOL., Vol. 32, pp. 257–264 (1983). Ethoxyresorufin O-deethylation is selectively catalyzed by P450 1A2. C. Gleizes, C. Eeckhoutte, T. Pineau, M. Alvinerie, and P. Galtier, "Inducing Effect of Oxfendazole on Cytochrome P4501A2 in Rabbit Liver", BIOCHEM. PHARMACOL. VOL. 41, pp. 1813–1820 (1991). Incubation of $^{14}$C-tacrine (5 μM) and chloroquine (100 μM) in primary suspensions of rat hepatocytes resulted in inhibition of tacrine irreversible binding as well as metabolism. Table 8 displays time course data for inhibition of binding.

TABLE 8

Effect of chloroquine (100 μM) on irreversible binding of tacrine-derived radioactivity to rat hepatocytes.

| | nmoles tacrine-equivalents bound per mg hepatic protein | |
|---|---|---|
| Time (min) | Tacrine | Tacrine + Chloroquine |
| 5 | 0.020* | 0.005 |
| 15 | 0.037 | 0.012 |
| 30 | 0.061 | 0.016 |
| 60 | 0.128 | 0.034 |
| 90 | 0.183 | 0.039 |
| 120 | 0.294 | 0.041 |
| 180 | 0.377 | 0.046 |

*N = 2

While the forms of the invention herein disclosed constitute presently preferred embodiments, many others are possible. It is not intended herein to mention all of the possible equivalent forms or ramifications of the invention. It is understood that terms used herein are merely descriptive rather than limiting and that various changes may be made without departing from the spirit or scope of the invention.

What is claimed is:

1. A method of treating Alzheimer's disease in a patient comprising administering to said patient an effective amount of tacrine in combination with a P450 1A2 oxidase inhibiting amount of a carbamoyl imidazole of Formula 7:

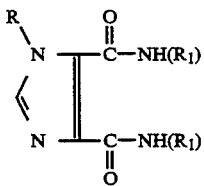

Formula 7 wherein R is alkyl of from 1 to 20 carbon atoms, and $R_1$ is independently alkyl of from 1 to 20 carbon atoms.

2. A method of treating Alzheimer's disease in a patient comprising administering to said patient an effective amount of tacrine in combination with a P450 oxidase inhibiting amount of a carbamoyl imidazole of Formula 7 whose onzymatic activity is induced by beta-naphthaflavone, 3-methylcholanthrene, arochlor, 2,3,7,8-tetrachloro-dibenzo-p-dioxin and isosafrole;

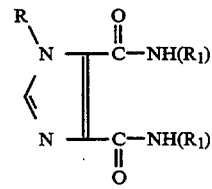

Formula 7 wherein R is alkyl of from 1 to 20 carbon atoms, and $R_1$ is independently alkyl of from 1 to 20 carbon atoms.

3. The method of claims 1 or 2 wherein R and $R_1$ are a lower alkyl group.

4. The method of claims 1 or 2 wherein the inhibitor is ethimizol.

5. A composition comprising tacrine and an effective oxidase inhibiting amount of a P450 1A2 inhibitor.

6. A composition comprising tacrine and an effective amount of an inhibitor of P450 oxidase whose enzymetic activity is induced by beta-naphthaflavone, 3-methylcholanthrene, arochlor, 2,3,7,8-tetrachlorodibenzo-p-dioxin and isosafrole.

7. The composition of claims 5 or 6 wherein the oxidase inhibitor is a carbamoyl imidazole Formula 7:

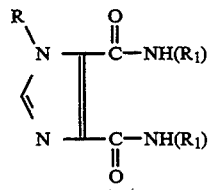

Formula 7 wherein R is alkyl of from 1 to 20 carbon atoms, and $R_1$ is independently alkyl of from 1 to 20 carbon atoms.

* * * * *